United States Patent [19]

Bell

[11] 4,046,143
[45] Sept. 6, 1977

[54] HEART PATIENT AID

[76] Inventor: Lawrence D. Bell, Hermitage Garden Apartments, Apt. C-204, Old Hickory, Tenn. 37138

[21] Appl. No.: 692,794

[22] Filed: June 4, 1976

[51] Int. Cl.² .............................................. A61F 13/00
[52] U.S. Cl. ..................................................... 128/133
[58] Field of Search ............................... 128/133–135; 119/96, 126, 128; 70/16–18

[56] References Cited

U.S. PATENT DOCUMENTS

| 647,735 | 4/1900 | Widmayer | 70/16 |
|---|---|---|---|
| 1,803,048 | 4/1931 | Allen | 119/128 |
| 1,845,338 | 2/1932 | Querna | 128/134 |
| 2,559,514 | 7/1951 | Parker | 128/133 |
| 2,650,590 | 9/1953 | Moore et al. | 128/134 |
| 3,535,718 | 10/1970 | Murcott | 128/133 X |
| 3,712,271 | 1/1973 | Greathouse | 128/134 |

*Primary Examiner*—Lawrence W. Trapp
*Attorney, Agent, or Firm*—Abe Hatcher

[57] ABSTRACT

Bar separating two leg cuffs prevents heart patients from crossing their legs.

10 Claims, 3 Drawing Figures

U.S. Patent      Sept. 6, 1977      4,046,143
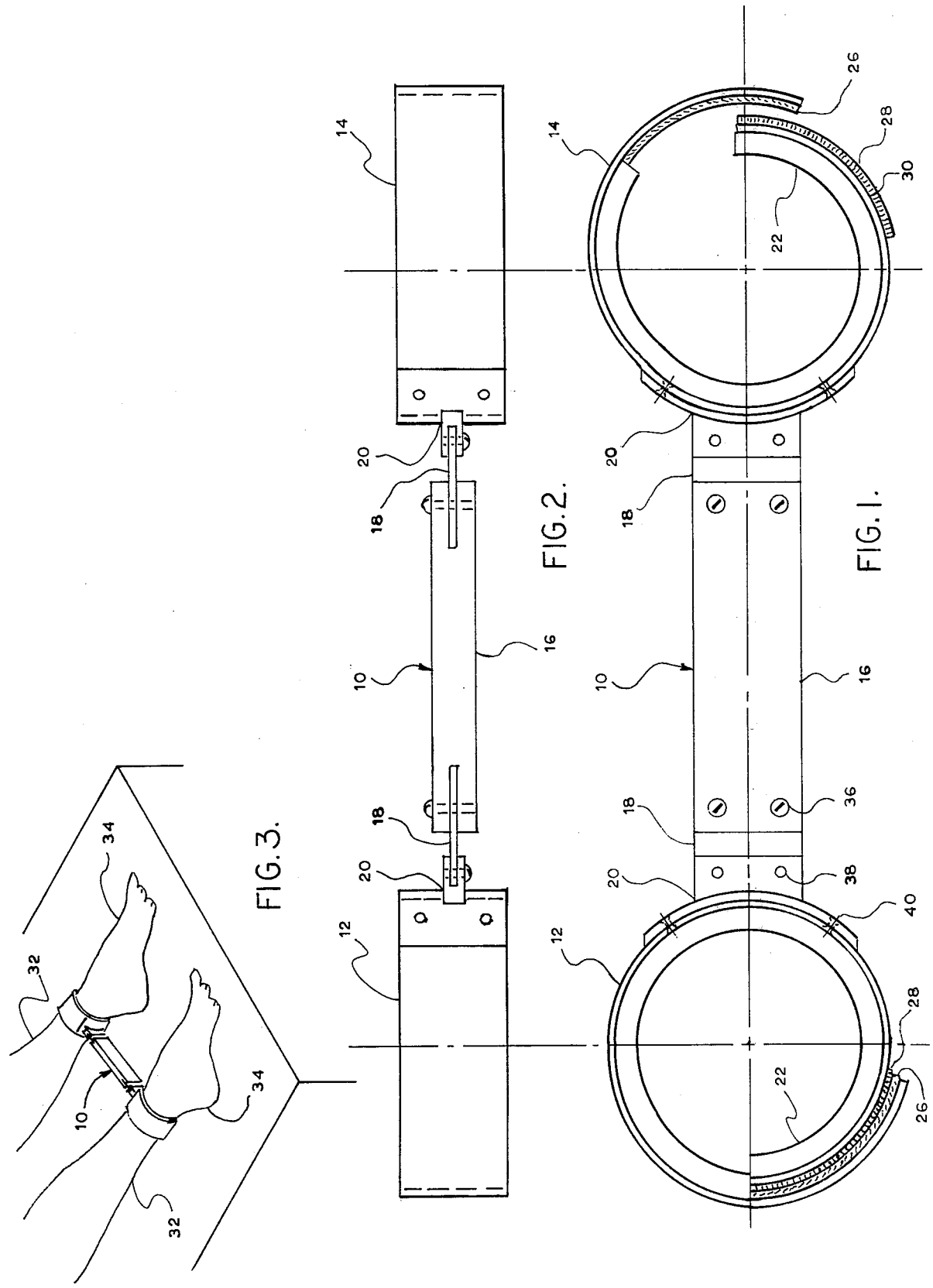

HEART PATIENT AID

BACKGROUND OF THE INVENTION

1. Field of the Invention

This invention relates to helping heart patients. More particularly, it relates to a device which prevents a person from crossing his legs.

2. Description of the Prior Art

U.S. Pat. Nos. 1,845,338; 2,650,590; 2,895,471; 3,324,851; 3,496,935 and 3,712,271 have to do with arm, leg and feet restraining devices and the like. However, none appears to be designed to prevent a person from crossing his or her legs. I have found that a device which does so, that is, prevents leg crossing, can be very helpful to heart patients, whether confined to bed or relaxing in a chair. Without hurting a patient, it helps permit free blood circulation, avoids clotting, and is particularly useful in cases of thrombophlebitis.

SUMMARY OF THE INVENTION

After extended investigation, I have found that leg crossing, not only by a patient in bed but also by one sitting in a chair, can be comfortably prevented by providing two leg cuffs separated by a bar and adapted to be placed slightly above one's ankles. My device, particularly inside the cuffs, may be made of rubberized plastic, foam rubber, for example, or any like materials which are capable of minimizing chafing and being sufficiently flexible to allow a patient wearing the device to exercise his feet and legs adequately and not be particularly discomforted while sleeping. Portions not touching the legs may be made of metal or plastic.

My leg separator may be a unitary item, that is, substantially all of one piece, although the bar joining the two cuffs may be a separate piece made of one or more parts and of the same or a different material, for example, a harder plastic or even wood or metal, for example, joined to the cuffs by nuts and bolts, rivets, screws, re-enforcing cross-pieces or the like, or by adhesive means, and the cuffs themselves may be made of metal, with the inside lined with a soft, non-chafing foam material such as foam rubber, polyurethane polyacrylate or the like. It is preferable that the joining bar be flexible, at least in part, so that a patient wearing the separator may at least move one leg upward or downward with respect to the other. The cuffs are preferably made so that the ends overlap at a point where they open outward simply by pulling open, for example, from a closed position in which they may be held by durable adhesive material either on the inside of the overlapping end or the outside of the overlapped end, or on both. Small wire-like prongs maybe used on the overlapping or overlapped ends to make them readily engageable and disengageable with the opposing overlapped or overlapping ends.

DESCRIPTION OF THE DRAWING AND PREFERRED EMBODIMENT

For a better understanding of the invention, reference will now be made to the drawing which forms a part hereof and illustrates an embodiment of the invention.

In the drawing,

FIG. 1 is a schematic illustration of a top or bottom view, partly in cross-section, of the leg separator of the invention, showing one cuff thereof partially open.

FIG. 2 is a schematic side view of the leg separator of FIG. 1.

FIG. 3 depicts schematically the legs of a patient held apart just above the ankles by a leg separator such as shown in FIGS. 1 and 2.

Leg separator 10 is made up of cuffs 12 and 14 separated by bar 16, which is joined to cuffs 12 and 14 by flexible sections 18 connected via parts 20 to inner ankle portions of said cuffs. Inner foam-cushioned or like layer 22 of cuffs 12 and 14 is adapted to rest snugly but comfortably against a patient's legs. Adhesive layer 26 sticks to pronged layer 28 having prongs 30 for holding tightly when layers 26 and 28 are fitted together so as to hold cuff 12, for example, as shown in FIG. 1, in closed position.

In FIG. 3 leg separator 10 is shown preventing legs 32 and feet 34 from being crossed.

In FIG. 1 are shown screws or bolts 36 and 38 holding section 18, which joins connecting bar 16 to cuffs 12 and 14, in place. Reinforcing pieces 40 are held against the outer layer of cuffs 12 and 14 at the juncture of bar 16 therewith via piece 20.

While the invention has been described in terms of preferred embodiments, the claims appended hereto are intended to encompass all embodiments which fall within the spirit of the invention.

Having thus described my invention and certain preferred embodiments thereof, I claim:

1. An article for holding legs of a heart patient apart near the ankles and preventing crossing of same comprising two circular members each having overlapping ends adapted to be pulled open outward upon exertion of slight force, said members being joined together by a connecting bar and having an insulating layer on the inside thereof for preventing chaffing of a person's legs when said members are closed therearound.

2. The article of claim 1 wherein said overlapping ends have adhesive layers for attachment to said overlapping ends.

3. The article of claim 1 wherein at least a part of said joining bar is flexible.

4. The article of claim 1 in unitary form as substantially one piece.

5. The article of claim 1 wherein said members and connecting bar are separate pieces joined together.

6. The article of claim 1 wherein said bar is joined at each end thereof to a member by means of an intermediate piece which projects into said bar and into an extension of said member.

7. The article of claim 6 wherein said intermediate piece is flexible and projections of said intermediate piece are held in place between portions of said bar and said extensions.

8. A process of alleviating circulation problems which comprises separating the legs of a patient at a point near the ankles thereof by closing circular members each having overlapping ends adapted to be pulled open outward upon exertion of slight force around each leg, said members being joined by a flexible separating bar and being lined inside with non-chafing material, and thereby preventing said patient from crossing his legs.

9. The process of claim 8 wherein said preventing crossing legs relieves a patient having thromophlebitis.

10. The process of claim 8 including providing at least a portion of said separating bar as flexible material.

* * * * *